(12) United States Patent
Stadtherr et al.

(10) Patent No.: US 9,867,912 B2
(45) Date of Patent: Jan. 16, 2018

(54) POLYURETHANE HAVING AN ANTITHROMBOGENIC COATING

(71) Applicant: pfm medical titanium gmbh, Nürnberg (DE)

(72) Inventors: Karin Stadtherr, Zenting (DE); Christof Schmid, Bad Abbach (DE); Karla Lehle, Wenzenbach (DE); Karin Lukas, Köfering (DE); Hanngörg Zimmermann, Gössweinstein (DE); Daniel Wehner, München (DE); Thomas Schmid, Schondorf (DE)

(73) Assignee: pfm medical titanium gmbh, Nürnberg (DE)

( * ) Notice: Subject to any disclaimer, the term of this patent is extended or adjusted under 35 U.S.C. 154(b) by 59 days.

(21) Appl. No.: 15/036,806

(22) PCT Filed: Nov. 12, 2014

(86) PCT No.: PCT/EP2014/074380
§ 371 (c)(1),
(2) Date: May 14, 2016

(87) PCT Pub. No.: WO2015/071313
PCT Pub. Date: May 21, 2015

(65) Prior Publication Data
US 2016/0279304 A1 Sep. 29, 2016

(30) Foreign Application Priority Data

Nov. 14, 2013 (EP) .................................... 13192956

(51) Int. Cl.
A61L 33/00 (2006.01)
(52) U.S. Cl.
CPC ....... *A61L 33/0029* (2013.01); *A61L 33/0094* (2013.01); *A61L 2400/18* (2013.01)
(58) Field of Classification Search
CPC ............. A61L 33/0029; A61L 33/0094; A61L 2400/18
See application file for complete search history.

(56) References Cited

U.S. PATENT DOCUMENTS

| 4,521,564 | A | 6/1985 | Solomon et al. |
| 5,132,108 | A | 7/1992 | Narayanan et al. |
| 6,491,965 | B1 | 12/2002 | Berry et al. |
| 2010/0129422 | A1* | 5/2010 | Han ........................ A61L 27/18 424/426 |

FOREIGN PATENT DOCUMENTS

| WO | 03034944 | 5/2003 |
| WO | 2011147409 | 12/2011 |

OTHER PUBLICATIONS http://publica.fraunhofer.de/documents/N-141596.html.
Trzaskowski M. et al., "Hydrogel Coatings for Artificial Heart Implants", The Challenges of Modern Technology 2 (1), 2011, pp. 19-22.
Sask, K.N., et al., "Modification of Polyurethane Surface with an Antithrombin-Heparin Complex for Blood Contact . . . ", Langmuir 2012, 28, pp. 2099-2106.
Du, Y.J. et al., "Protein Adsorption on Polyurethane Catheters Modified with a Novel Antithrombin-Heparin Covalent Complex", Journal of Biomedical Materials Research Part A, vol. 80A, Issue 1, 2007, pp. 216-225.
Ademovic Zahida, "Oberflächenmodifizierung von Polyvinylidenfluorid zur Minimierung der Proteinadsorption", 2002, Institute of Technology Aachen.

* cited by examiner

*Primary Examiner* — Robert Jones, Jr.
(74) *Attorney, Agent, or Firm* — Boyle Fredrickson S.C.

(57) ABSTRACT

The invention concerns polyurethane (PUR) having an antithrombogenic coating, wherein the antithrombogenic coating comprises at least one antithrombogenic substance covalently bound to a surface of the PUR via at least two bonds, wherein a first of said bonds is an amide bond between the surface of the PUR and a polyethyleneimine (PEI) and a second of said bonds is between the PEI and the antithrombogenic substance, wherein the surface of the PUR had been activated by use of a carbon dioxide plasma or a plasma modified by addition of carbon dioxide before the first of said bonds was formed.

20 Claims, 7 Drawing Sheets

POLYURETHANE HAVING AN ANTITHROMBOGENIC COATING

FIELD OF THE INVENTION

The invention concerns a polyurethane (PUR) having an antithrombogenic coating, wherein the antithrombogenic coating comprises at least one antithrombogenic substance covalently bound to a surface of the PUR.

BACKGROUND OF THE INVENTION

From http://publica.fraunhofer.de/documents/N-141596.html it is known that polycarbonate-urethanes are used in medical technology because of their bio- and hemo-compatibility, biostability, toughness and gliding properties in highly stressed implants. A high degree of ability to modify the surface allows the application of antimicrobial or antithrombogenic coatings.

Trzaskowski M., et al., The Challenges of Modern Technology 2 (1), 2011, pages 19 to 22 discloses a polyvinylpyrrolidone hydrogel coating on a surface of polyurethane for an artificial heart implant. Polyvinylpyrrolidone is a highly hydrophilic polymer that forms hydrogels in water. It is expected to increase the biocompatibility of the coated material and prevent blood from clotting on the surface of the PUR. Furthermore, it is disclosed that previously hemocompatibility has been improved by coating of PUR surfaces with proteins that actively prevent blood from coagulation, e.g. heparin, urokinase or thrombomodulin. Insufficient durability of these modifications is mentioned as their main disadvantage.

Sask, K. N., et al., Langmuir 2012, 28, pages 2099 to 2106 discloses the modification of polyurethane surface with an antithrombin-heparin complex for blood contact. It is described to use isocyanate chemistry for covalent coupling of polyethylene oxide (PEO) to the surface of the polyurethane. Subsequently the antithrombin-heparin complex is covalently coupled to the PEO.

A covalent coating of polyurethane catheters with an antithrombin-heparin complex via PEO is known from Du, Y. J., et al., Journal of Biomedical Materials Research Part A, Volume 80 A, Issue 1, 2007, pages 216 to 225.

From U.S. Pat. No. 6,491,965 B1 a medical device comprising glycosaminoglycan-antithrombin III/heparin cofactor II conjugates is known. The conjugates are covalently attached to a polymer of the device. The polymer may be polyurethane or polycarbonate-polyurethane. The device may be a cardiac catheter, a cardiopulmonary bypass circuit, a dialysis circuit or an in vivo prosthesis.

WO 2011/147409 describes a coating of endoprostheses with a coating consisting of a tight mesh of polymer fibres. The polymer may be polyurethane. The endoprostheses may comprise an anti-restenotic active substance such as an antithromboticum, e. g. antithrombin. The active substance may be contained in the mesh of polymer fibres in covalently, adhesively or ionically bound form.

From WO 03/034944 A1 a coating of stents for preventing restenosis is known. The coating may contain an antithrombotic active substance such as antithrombin. The stent is covered with a first hemocompatible coating and at least one second coating comprising the active substance. The hemocompatible coating may consist of heparin, oligo- and polysaccharides, polyacrylic acid, polyvinylpyrrolidone and other polymers.

From the doctoral thesis "Oberflächenmodifizierung von Polyvinylidenfluorid zur Minimierung der Proteinadsorption", Ademovic Zahida, 2002, Institute of Technology Aachen it is known to bind polyacrylic acid to the surface of PVDF and to bind polyethyleneimine (PEI) to the carboxy groups of the polyacrylic acid via the use of carbodiimide. Subsequently polyethylene glycol aldehydes, carboxymethylated dextran or carboxymethylated hydroxyethyl starch were covalently coupled to the amino groups of PEI. The aim of this coating was to generate a surface coating that reduces or prevents non-specific protein binding and the resulting cell adhesion. Coating with polyacrylic acid requires a long-term incubation at about 90° C. This may result in a change of the properties of the coated substrate. A lower temperature results in an ineffective coating.

From U.S. Pat. No. 4,521,564 an antithrombogenic polyurethane polymer is known. The polymer comprises a polyurethane substrate, a polymeric amine covalently bonded to said polyurethane substrate and an antithrombogenic agent covalently bonded to said polymeric amine. The polymeric amine may be polyethyleneimine.

From U.S. Pat. No. 5,132,108 a medical device having a biocompatible polymeric surface is known. Said biocompatible polymeric surface comprises a surface which has been modified by subjecting the polymeric surface to radiofrequency discharge treatment within a plasma medium having between about 40 and about 90 volume percent water vapor, the balance of that plasma medium being between about 10 and about 60 volume percent oxygen based upon the total volume of plasma medium. The plasma treatment is followed by treatment with a coupling agent and a spacer component having amine groups forming covalent linkages with the polymeric surfaces which had been subjected to radiofrequency discharge treatment with said plasma medium, and then by treatment with an antithrombogenic, fibrinolytic or thrombolytic agent having acid functionality contacting and covalently bonding with the spacer component-treated polymeric surface. The polymeric surface may be a polyurethane surface. The spacer molecule which provides reactive sites for attachment of the antithrombogenic agent may be polyethyleneimine. Covalent linkages between the reactive sites on the polymeric surface and the amine groups of the spacer molecule may be provided by using a suitable coupling agent such as 1-ethyl-3-(3-dimethylaminopropyl)-carbodiimide hydrochloride (EDC) or dicyclohexyl carbodiimide (DCC). The plasma medium is provided within a chamber. Air or other gas is first evacuated from the radiofrequency treatment chamber until virtually no air or other gas remains therewithin. Then the water vapor is pumped or otherwise injected into the chamber and a radio frequency electric field is generated within the reactor chamber, thereby inducing treatment of the polymeric surface.

SUMMARY OF THE INVENTION

The problem to be solved by the present invention is to provide an alternative material suitable for the production of a medical device to be inserted temporarily or permanently into the bloodstream or the body of a mammal, in particular a human being. Furthermore, a medical use of the material, a medical device and a method of producing the material shall be provided.

According to the invention, PUR having an antithrombogenic coating is provided. The antithrombogenic coating comprises at least one antithrombogenic substance covalently bound to a surface of the PUR via at least two bonds, wherein a first of said bonds is an amide bond between the surface of the PUR and a polyethyleneimine (PEI) and a second of said bonds is between the PEI and the antithrombogenic substance. The second bond can be an amide bond, too. The surface of the PUR had been activated by use of a plasma before the first of said bonds was formed. The plasma is a carbon dioxide plasma or a plasma modified by addition of carbon dioxide. The modification of the plasma results not only in an increased amount of PEI that is bound to the PUR surface but also in an increased antithrombogenic effect. The reason for this effect is not known. With respect to the increased amount of bound PEI it is assumed that the addition of the carbon dioxide results in the formation of additional carboxy groups on the surface of the PUR. The carboxy groups can be used for covalent binding of the PEI. Furthermore, it has been found that the combination of PEI and the antithrombogenic substance is very advantageous. PEI forms a hydrogel when contacted with water or a body fluid. In combination with the PEI and the antithrombogenic substance the plasma treatment shows a positive antithrombogenic effect and an antiadhesive effect on thrombocytes as well as an adhesion supporting effect on endothelial cells.

The carbon dioxide plasma and the plasma modified by addition of carbon dioxide may be a low pressure plasma, in particular an atmospheric-pressure plasma, i.e. a plasma in which the pressure matches or approximately matches that of the surrounding atmosphere. It may be generated by means of a high-voltage discharge at a frequency of 10 to 250 kHz. The plasma to be modified by addition of carbon dioxide may be a nitrogen plasma ($N_2$-plasma) or an argon plasma.

The PUR according to the invention overcomes the problems of formation of thrombi caused by medical devices to be implanted. It has been found that it is very effective in inhibiting the triggering of blood coagulation, adhesion of thrombocytes and the activation of thrombocytes and leukocytes. Furthermore, it has been found to inhibit colonization with bacteria and the resulting formation of biofilm on the medical devices to be implanted. The formation of biofilm, in particular caused by colonization by *Staphylococcus epidermidis*, is a main cause of implant associated chronic infections. Since these chronic infections cannot be successfully treated by antibiotics in most cases there is an urgent need for surfaces of implants which prevent or inhibit the formation of biofilms. The PUR according to the invention is very effective in inhibiting the adhesion of bacteria, the growth of bacteria and the formation of biofilms.

The PUR may be a PUR elastomer. PUR elastomers are multi-phase block copolymers that consist of alternating blocks of "hard" and "soft" segments and are thus referred to as segmented polymers. In particular the PUR may be an elastomeric polycarbonate based PUR. Such a PUR can be synthesized from polycarbonate polyol, methylene diisocyanate, ethylene diamine, and diaminocyclohexane. The polycarbonate polyol may be polycarbonate glycol. The PUR may be synthesized in dimethylacetamide (DMAC) as a solvent. DMAC can also be used to dissolve the PUR for shaping it as desired. The elastomeric PUR can be purchased from AdvanSource Biomaterials, 229 Andover Street, Wilmington, Mass. 01887, USA under the names ChronoFlex AR®, ChronoFlex AR-LT®, ChronoFlex C® or ChronoSil®. It can also be purchased from The Lubrizol Corporation, 29400 Lakeland Boulevard, Wickliffe, Ohio 44092, USA under the name Carbothane® TPU or from DSM Biomedical B. V., Koestraat 1, 6167 R A Geleen, The Netherlands under the names CarboSil® TSPCU, BioSpan® SPU, Bionate® PCU and Elasthane™ TPU. A further PUR that can be used is Vasomer® from B. Braun Melsungen AG.

In one embodiment the PEI is branched or a dendrimer. In this case the number of bonds, in particular amide bonds, by which the antithrombogenic substance can be bound and therewith the antithrombogenic effect can be enormously increased.

The antithrombogenic substance may be heparin modified to comprise a reactive group in unbound condition or antithrombin III (AT III) or any other antithrombogenic substance having at least one carboxy group, ketone group, aldehyde group or amino group in unbound condition. The reactive group of the modified heparin may be a carboxy group, ketone group, aldehyde group or amino group. Heparin can be modified by reaction with $NaNO_2/HCl$. In this reaction the heparin molecule is shortened and an aldehyde group is formed. This modified heparin molecule can be bound via the aldehyde group to an amino group of the PEI by reductive amination by means of $NaBH_3CN$. If the antithrombogenic substance comprises an amino group the binding to an amino group of the PEI can be achieved by a coupling via glutardialdehyde. The man skilled in the art knows further methods and mechanisms to couple the mentioned reactive groups to an amino group of the PEI. In combination with PEI heparin as well as AT III are very effective in inhibition of thrombus formation.

The invention also concerns a PUR according to the invention for use as a medicament.

The invention also concerns a PUR according to the invention for use in the treatment of thrombosis or a risk of getting thrombosis. The PUR according to the invention can inhibit thrombus formation and the triggering of blood coagulation. It can also inhibit adhesion of thrombocytes and the activation of thrombocytes and leukocytes.

The invention also concerns a medical device to be inserted or contacted temporary or permanently into or with a bloodstream or to be inserted temporary or permanently into a body of a mammal or a human being, wherein a surface of said medical device comprises the PUR according to the invention. The medical device may be a catheter, a tube for the flow-through of blood, an artificial cardiac valve, an artificial heart, or a substitute for a bone or a joint or a part of a bone or a joint.

The invention also concerns a method of producing the PUR according to the invention comprising the following steps:
  a) Activation of the PUR surface,
  b) first coupling, wherein the PEI is coupled to the PUR surface, and
  c) second coupling, wherein the antithrombogenic substance is coupled to the PEI.

The first coupling and/or the second coupling may be in each case a carbodiimide-mediated coupling. The carbodiimide-mediated coupling requires in each case the presence of an amino group and a carboxy group. In case of the first and the second coupling the amino group is provided by the PEI. The activation of the surface comprises the formation of radicals on the surface of the PUR followed by formation of carboxy groups. This may occur by reaction with $O_2$ or $CO_2$ present in the air. The method allows a covalent coupling of substances to PUR without the disadvantage of exposure to a relative high temperature as required for an effective coupling of polyacrylic acid.

The activation is performed by use of a plasma, i.e., an ionized gas. The plasma may be a cold plasma. A cold plasma is a plasma in which only a small fraction of the gas molecules are ionized.

It has been shown that the activation of the PUR surface is sufficient to generate enough carboxy groups on the surface to which PEI can covalently be bound via amide bonds. The plasma may be a carbon dioxide plasma, a nitrogen plasma or an argon plasma. If the plasma is not a carbon dioxide plasma it is modified by addition of carbon dioxide. The carbon dioxide may be added just by addition of air or by addition of pure or medical grade carbon dioxide. The modification of the plasma increases the amount of PEI that can be bound to the PUR surface. It is assumed that the addition of the carbon dioxide results in the formation of additional carboxy groups on the surface of the PUR. The carboxy groups can be used for covalent binding of the PEI. Furthermore, it has been found that the modification of the plasma increases the antithrombogenic effect of the PUR according to the invention.

According to a further embodiment of the method the PUR surface is exposed to air or oxygen between steps a) and b). This exposure allows additional covalent binding to the PUR surface. It is assumed that the effect of this incubation is that hydroperoxides are generated on the surface of the PUR.

The PUR surface may be incubated in water, a buffer, or a saline solution, in particular an isotonic saline solution, between steps a) and b). In case the PUR surface is exposed to air or oxygen between steps a) and b) the PUR surface is incubated in the water, the buffer, the saline solution, or the isotonic saline solution between steps a) and b) and after the exposure to air or oxygen. By this incubation the surface of PUR changes and the PUR swells. The PUR becomes turbid in a subsequent washing step in deionized water. The modified surface allows an increased binding of PEI. The incubation may be performed at room temperature but the effect is enhanced if the temperature is slightly raised, e. g. to about 50° C.

For increasing the amount of covalently bound PEI step b) can be performed at least twice.

The first and/or the second coupling can be performed by use of N-Hydroxysuccinimide (NHS) and N,N'-Dicyclohexylcarbodiimide (DCC) or 1-Ethyl-3-(3-dimethylaminopropyl)carbodiimide (EDC). The EDC may be obtained and applied as the hydrochloride of EDC. This carbodiimide-mediated coupling has been shown to be very effective. The inventors found that the PUR can be dried after step c), in particular after rinsing it with demineralized water. After rewetting the dried PUR it has still a very good antithrombogenic activity and prevents adhesion of proteins and cells. The drying facilitates the handling, storage and distribution of the PUR according to the invention.

BRIEF DESCRIPTION OF THE DRAWINGS

Embodiments of the invention.

DETAILED DESCRIPTION OF THE PREFERRED EMBODIMENTS

To produce the PUR according to the invention ChronoFlex AR® purchased from AdvanSource Biomaterials was used to produce small discs of PUR. The discs were washed for 10 minutes in pure ethanol or isopropanol and then dried for at least 24 hours at room temperature. Afterwards the discs were activated by use of a cold nitrogen plasma generated at 4.5 kV with a gas flow of 20 Nl (normal liter) per minute to which medical grade carbon dioxide was added with a gas flow of 1.5 to 2.0 Nl/min. The plasma beam was moved with a velocity of 5 cm/min over the PUR surface. After the plasma treatment the discs were exposed to air for 45 minutes at room temperature. Afterwards the discs were incubated for two hours at 50° C. in an isotonic saline solution. During this treatment the surfaces of the discs changed. Discs activated with plasma became turbid in a subsequent washing step in deionized water whereas none-activated discs remained clear during the same procedure.

Figure 1:
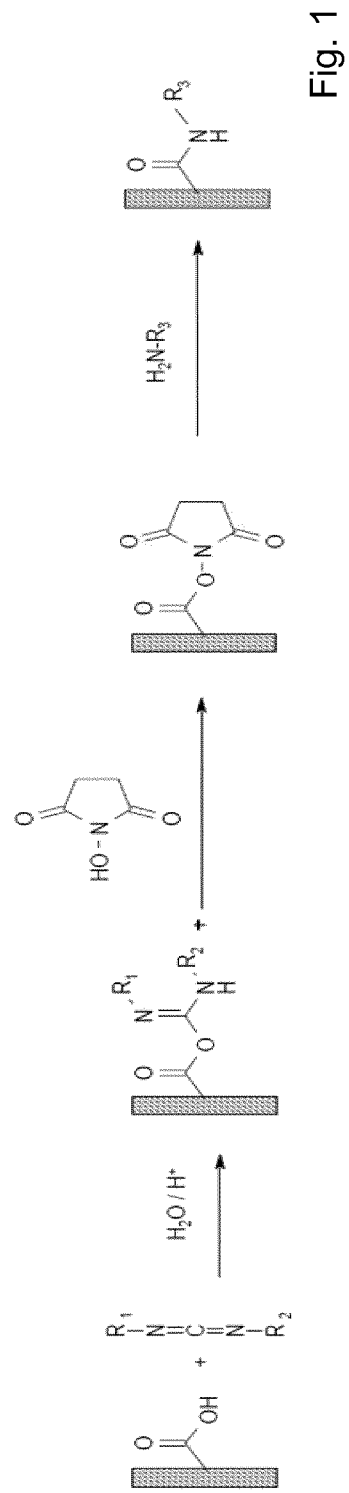
FIG. 1 shows a schematic presentation of the carbodiimide-mediated coupling of polyethyleneimine.
Figure 2:
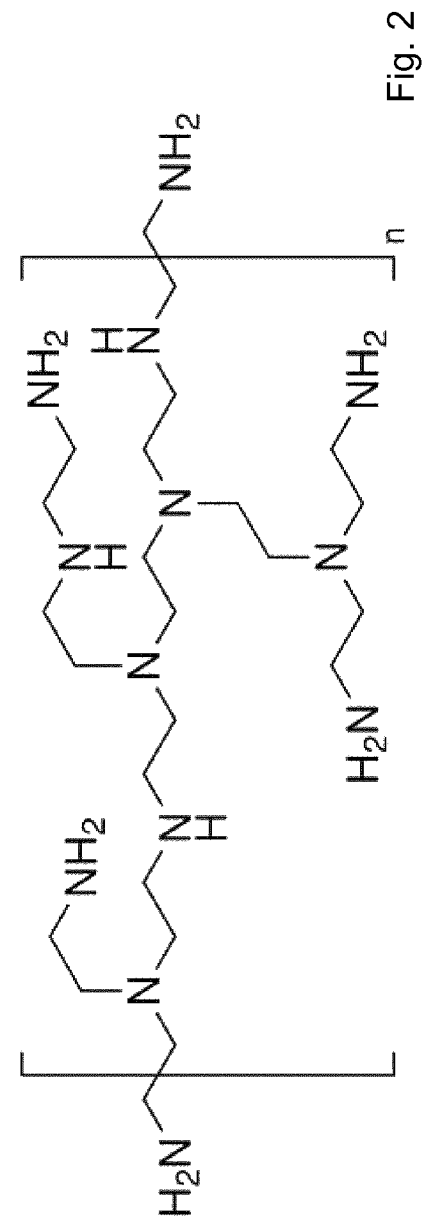
FIG. 2 shows a formula of branched PEI.

After rinsing the discs with deionized water the PUR was incubated for 20 minutes in 0.1 M 1-Ethyl-3-(3-dimethylaminopropyl) carbodiimide (EDC) and 0.1 M N-Hydroxysuccinimide (NHS) in water. Afterwards the discs were rinsed with demineralized water again and immediately incubated with 0.3% branched polyethyleneimine in carbonate buffer for two hours at 50° C. During this procedure polyethyleneimine was covalently bound via an amino group to a —COOH group of the PUR. The reaction is schematically shown in FIG. 1. FIG. 2 shows a formula of the branched polyethyleneimine (PEI). The resulting product PUR-PEI was rinsed with demineralized water. 4 IU/ml of antithrombin III were activated for 20 minutes with 0.2 M EDC and 0.1 M NHS in an aqueous solution. Afterwards three parts of carbonate buffer were added to one part of this solution. The PUR-PEI is incubated in the resulting solution for at least 19 hours at 4° C. At the end of the reaction the resulting PUR-PEI-AT III discs were rinsed with demineralized water and dried at 4° C.

Figure 3:
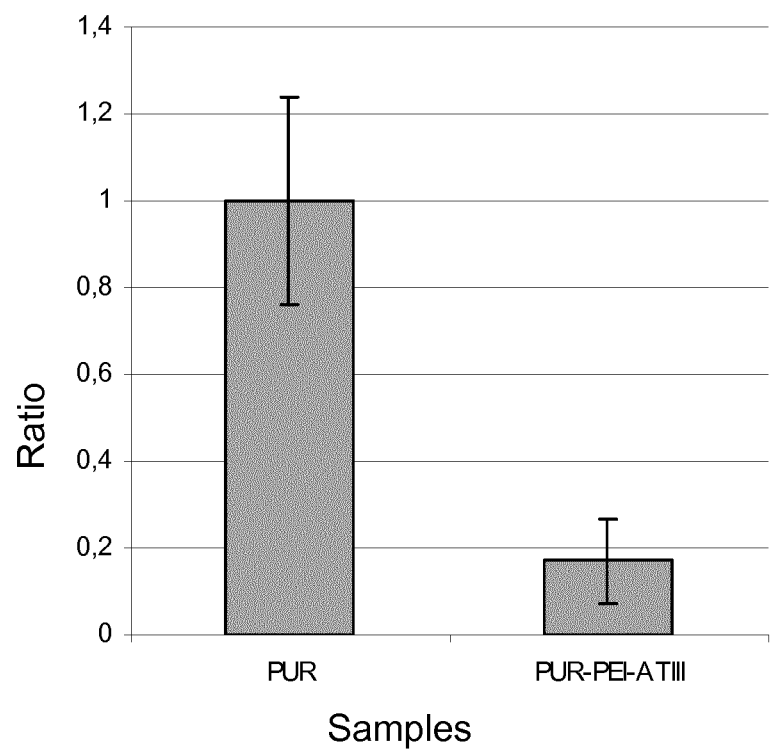
FIG. 3 shows a chart of the adhesion of *Staphylococcus epidermidis* (STEP) on PUR and PUR-PEI-AT III.

The first stage of biofilm formation is the adhesion of bacteria on the surface of a material and proliferation of the bacteria. *Staphylococcus epidermidis* is a bacterium that can form biofilms. PUR-PEI-AT III and PUR were tested with respect to adhesion and proliferation of *Staphylococcus epidermidis* (STEP). For this purpose the PUR and PUR-PEI-AT III discs were incubated for 30 minutes at 37° C. in a suspension of bacteria. Afterwards the discs were washed five times. Then the side of the discs that was exposed to the bacteria was laid on a blood agar plate and remained on the blood agar. Afterwards the blood agar was incubated over night at 37° C. Then the discs were removed. At the positions at which bacteria were applied to the blood agar they began to proliferate and formed cavities in the blood agar that could be counted as colony forming units to quantify the number of bacteria that adhered on the discs. The resulting ratio of bacteria adhering on PUR to bacteria adhering to PUR-PEI-AT III is shown in FIG. 3. In the experiment two different charges of PUR and PUR-PEI-AT were examined in two independent assays, four times each. This shows that the adhesion of STEP to PUR-PEI-AT III is reduced by about 80% with respect to the adhesion to PUR.

Figure 4:
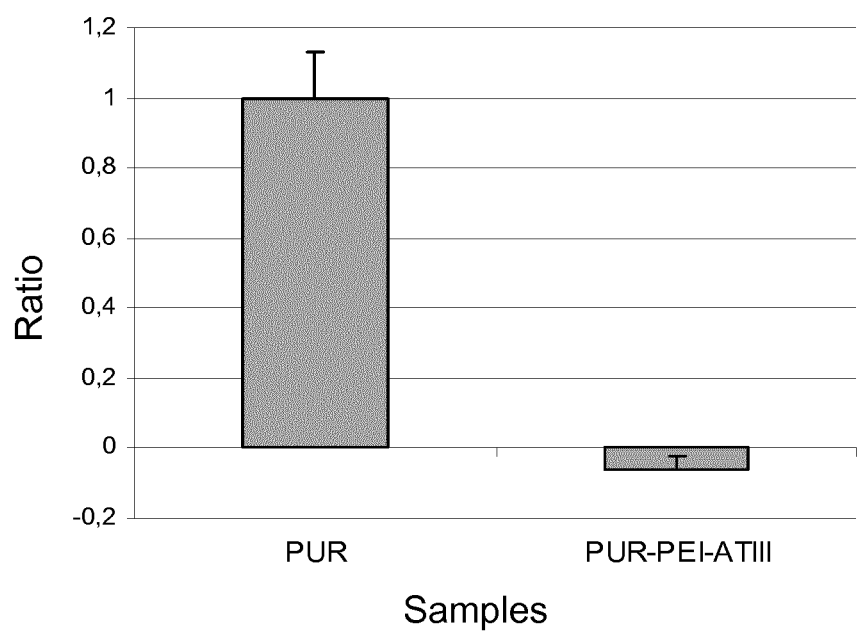
FIG. 4 shows a chart of the proliferation of STEP after 8 hours of incubation on PUR and PUR-PEI-AT III.
Figure 5:
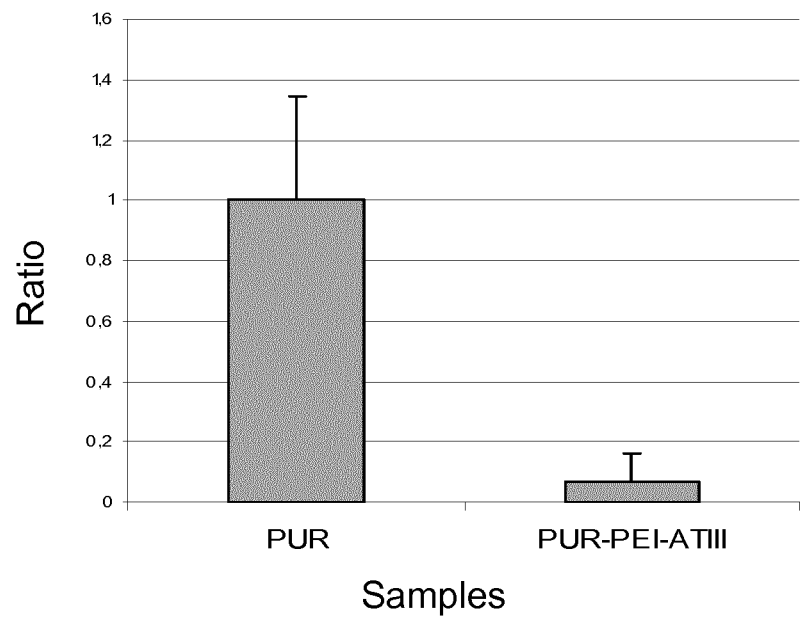
FIG. 5 shows a chart of the proliferation of STEP after 120 hours of incubation on PUR and PUR-PEI-AT III.

To examine the proliferation of bacteria, bacteria were grown on PUR and PUR-PEI-AT III discs for 8 hours and 120 hours at 37° C. Afterwards bacteria were fixed by use of pure methanol and stained with 0.2% crystal violet. After several washing steps crystal violet was dissolved from the bacteria by use of ethanol. Quantification was performed by measuring absorbance at 595 nm. The results are shown in FIGS. 4 and 5. In early stages of proliferation few bacteria detached from the discs. In later stages of biofilm formation pieces of the biofilm detached from the discs. In both experiments two different charges of PUR and PUR-PEI-AT III were tested in independent assays (three times each).

The results show that PUR-PEI-AT III in contrast to PUR does not allow a significant proliferation of STEP.

Figure 6:
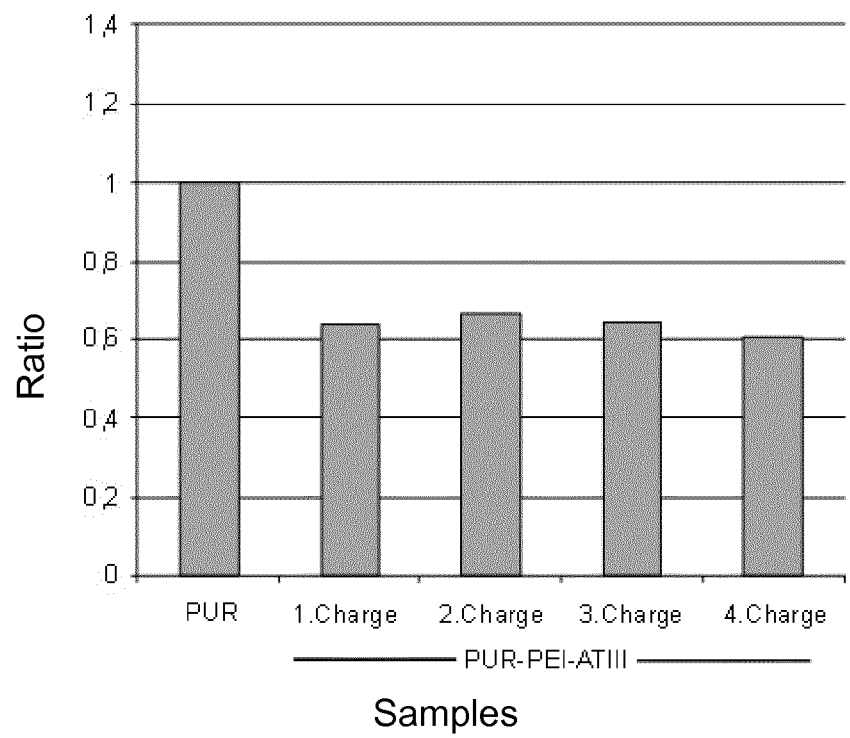
FIG. 6 shows a chart of the formation of coagulates induced by PUR and four charges of PUR-PEI-AT III.

In a further experiment PUR and PUR-PEI-AT III discs were incubated with EDTA-blood (reactivated by use of $CaCl_2$) for two days. During this time a thrombus could form on the surface of the discs. After the two days the discs were removed from the blood, washed thoroughly and weighed. The results obtained with PUR and four different charges of PUR-PEI-AT III are shown in FIG. 6. The value obtained for PUR is set a 1.0 and the other values are given in relation to this value. The results show a 40% reduction of coagulate formation upon contact with PUR-PEI-AT III compared to PUR.

Figure 7:
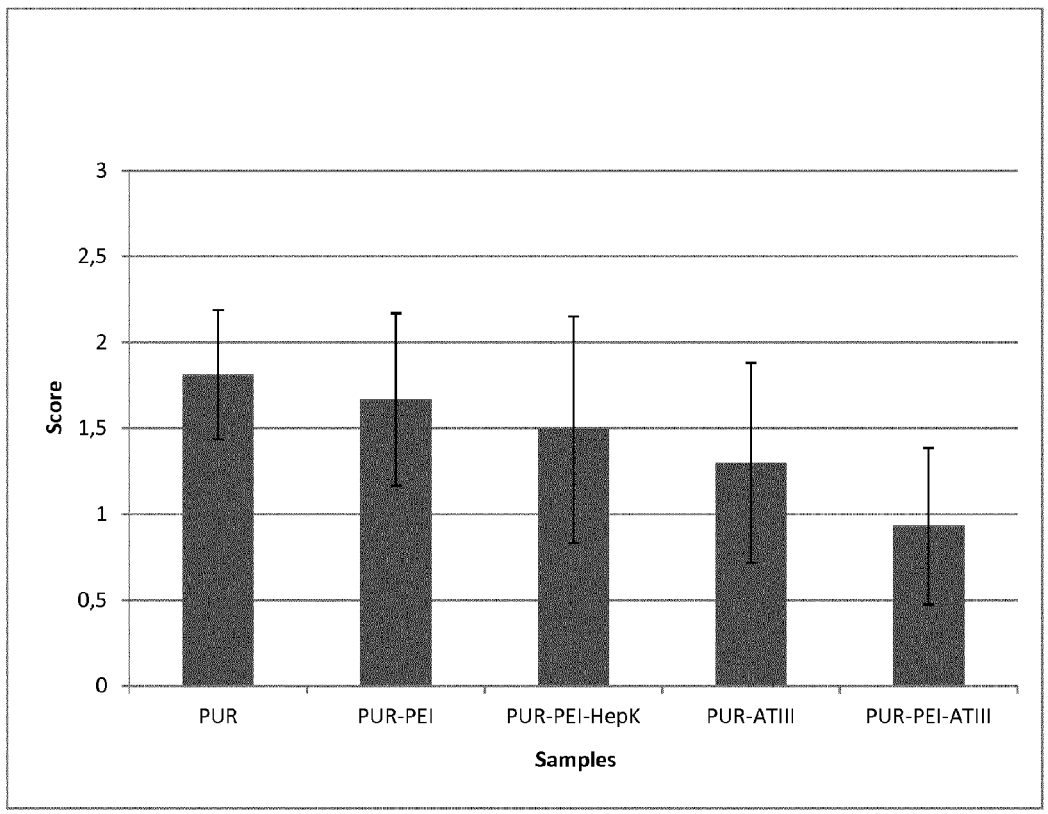
FIG. 7 shows a chart of thrombocytes binding to PUR and PUR with several coatings.

In a further assay adhesion of thrombocytes was examined. For this purpose uncoated PUR discs or PUR discs coated with PEI, PEI-heparin K (PEI-HepK), AT III and PEI-AT III were incubated in a thrombocyte suspension at 37° C., 5% $CO_2$ for 60 minutes. Afterwards adhering thrombocytes were fixed, permeabilized and stained with rhodamine-phalloidin. Results were determined by fluorescence microscopy and scoring. Thrombocytes of five different donors were examined. The results are shown in FIG. 7. Four arbitrarily selected fields of view per disc were analyzed by three independent persons. Score 1 means that less than 20% of the surface was covered with thrombocytes. Score 2 means that 20% to 50% and score 3 that more than 50% of the surface was covered with thrombocytes.

Figure 8:
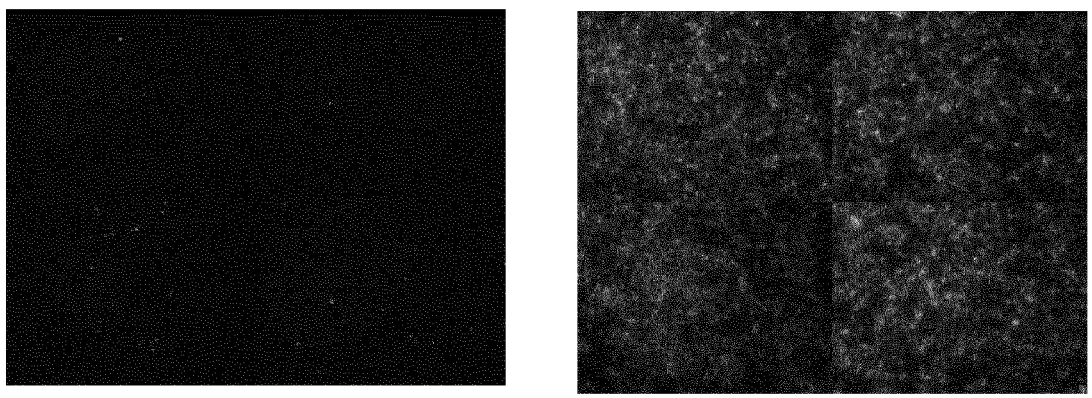
FIG. 8 shows photomicrographs of PUR and PUR-PEI-AT III surfaces after incubation with thrombocytes in suspension, washing and rhodamine-phalloidin staining of adhering thrombocytes.

FIG. 8 shows on the left panel four fields of view of PUR-PEI-AT III discs and on the right panel four fields of view of PUR discs after thrombocytes adhesion and rhodamine-phalloidin-staining.

The results show that PUR-PEI-AT III is repulsive for thrombocytes. The results from FIG. 7 also show that the effect is not only an effect of PEI and not only an effect of AT III but a synergistic effect of the combination of PEI and AT III.

Figure 9:
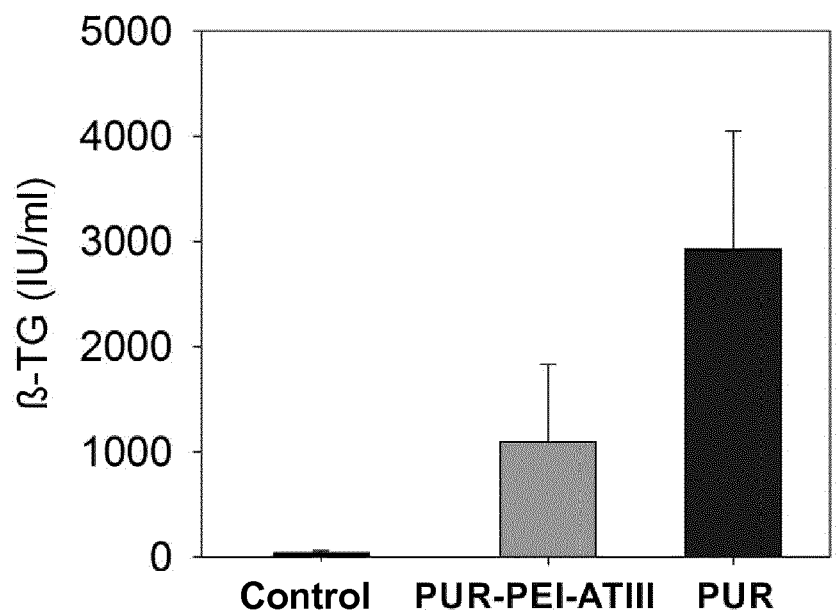
FIG. 9 shows a chart of the activation of thrombocytes before and after 90 minutes of contact with PUR and PUR-PEI-AT III.

In a dynamic approach tubes coated with PUR-PEI-AT III on their inner surface were filled with heparinized blood of five different donors. The tubes were rotated and therewith the blood was exposed to defined shear forces. The results are compared to the results obtained with untreated heparinized blood. The inner surface of the tubes was examined by use of electron microscopy. The experiments showed that much less thrombocytes adhered to tubes coated with PUR-PEI-AT III than to uncoated PUR tubes. In this approach activation of thrombocytes by measuring of released β-thromboglobulin (β-TG) has been determined. β-thromboglobulin is stored in thrombocytes and released after activation. The results are shown in FIG. 9. FIG. 9 shows β-thromboglobulin release before (control) and after 90 minutes of contact with the uncoated (PUR) or coated (PUR-PEI-AT III) tubes in the dynamic approach. Each value has been determined five times. FIG. 9 shows that thrombocytes were much less activated by PUR-PEI-AT III compared to PUR.

Figure 10:
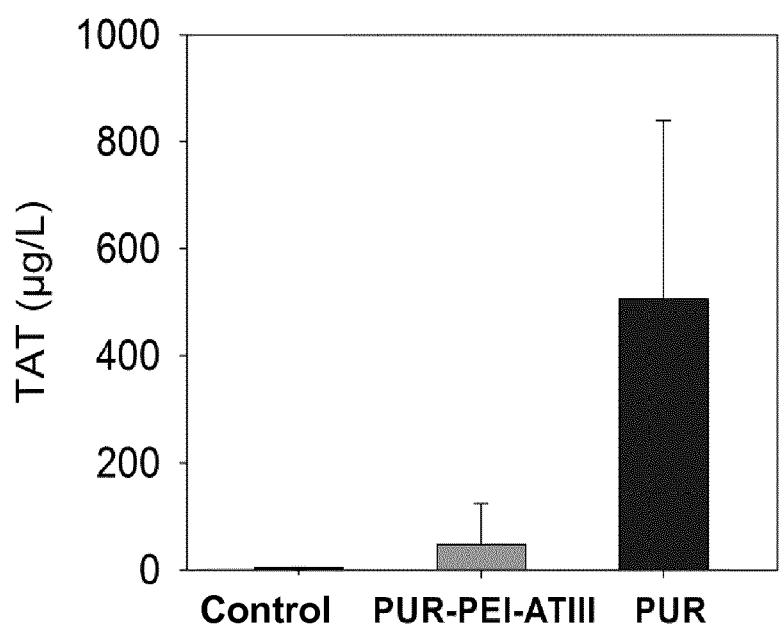
FIG. 10 shows a chart of the thrombin content of whole blood before and after 90 minutes of contact with PUR and PUR-PEI-AT III.

In a further assay the extend of thrombin formation is examined by determining the concentration of thrombin in whole blood before (control) and after 90 minutes of incubation in the dynamic approach via measurement of the formation of thrombin-antithrombin III (TAT)-complex. Results of five independent measurements are shown in FIG. 10. This shows that PUR-PEI-AT III significantly inhibits thrombin formation and therewith thrombus formation compared to PUR.

Figure 11:
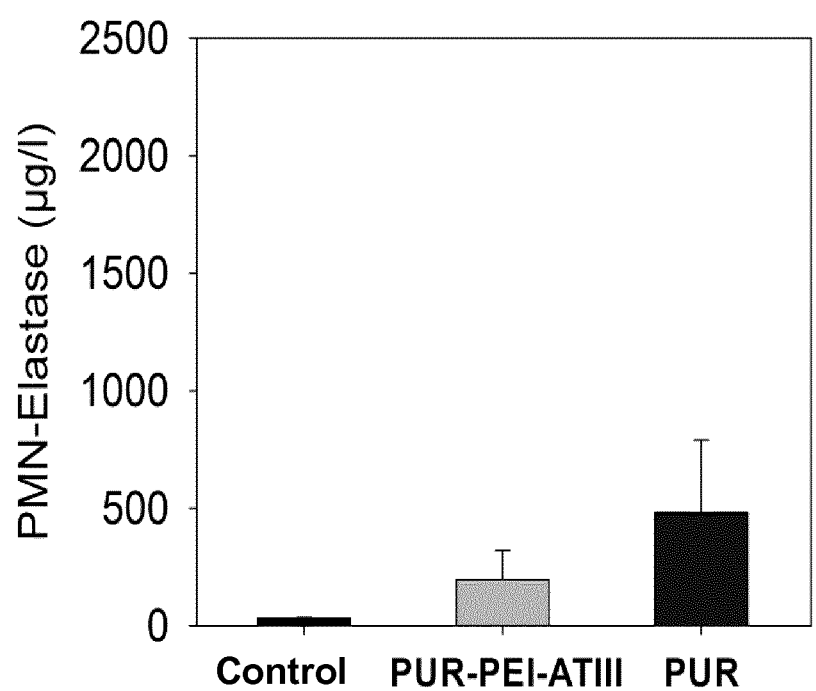
FIG. 11 shows a chart of the activation of leukocytes in whole blood before and after 90 minutes of contact with PUR and PUR-PEI-AT III.

In a further experiment activation of leukocytes was examined. PMN-elastase present in neutrophil granulocytes is released during inflammation. Release of PMN-elastase shows leukocyte activation. PMN-elastase concentration was determined in whole blood before (control) and after 90 minutes of incubation in the dynamic approach in five independent determinations. The results are shown in FIG. 11. This shows that PUR-PEI-AT III inhibits leukocyte activation in this dynamic approach significantly when compared to PUR.

Another assay was performed to compare the effect of different plasmas on thrombus formation. For this purpose PUR was prepared as described above. However, the PUR was either not activated with a plasma (in case of "control" and "without plasma" according to FIG. 12) or activated with an argon-plasma, an $N_2$-plasma or with a $CO_2$-modified $N_2$-plasma. The argon-plasma was a cold argon-plasma generated at 4.5 kV with a gas flow of 10 Nl per minute. The nitrogen-plasma was a cold nitrogen-plasma generated at 4.5 kV with a gas flow of 20 Nl per minute. In case of the modified $N_2$-plasma medical grade carbon dioxide was added to the nitrogen gas flow of 20 Nl per minute with a gas flow of 1.7 Nl per minute. In every case of plasma treatment the plasma beam was moved with a velocity of 5 cm/min over the PUR surface. In all cases except the case "without plasma and without NaCl" the discs were incubated for two hours at 50° C. in isotonic saline solution. After rinsing the discs with deionized water the PUR was incubated for 20 minutes in 0.1 M EDC and 0.1 M NHS in water. Afterwards the discs were rinsed with demineralized water again and immediately incubated with 1 IU/ml AT III in 0.1 M carbonate buffer, pH 8.4 over night at 4° C. Afterwards the discs were rinsed with demineralized water and dried at 4° C.

In case of a control the only treatment of the discs consisted in washing the discs for 10 minutes in pure ethanol and drying the discs in air at room temperature.

Figure 12:
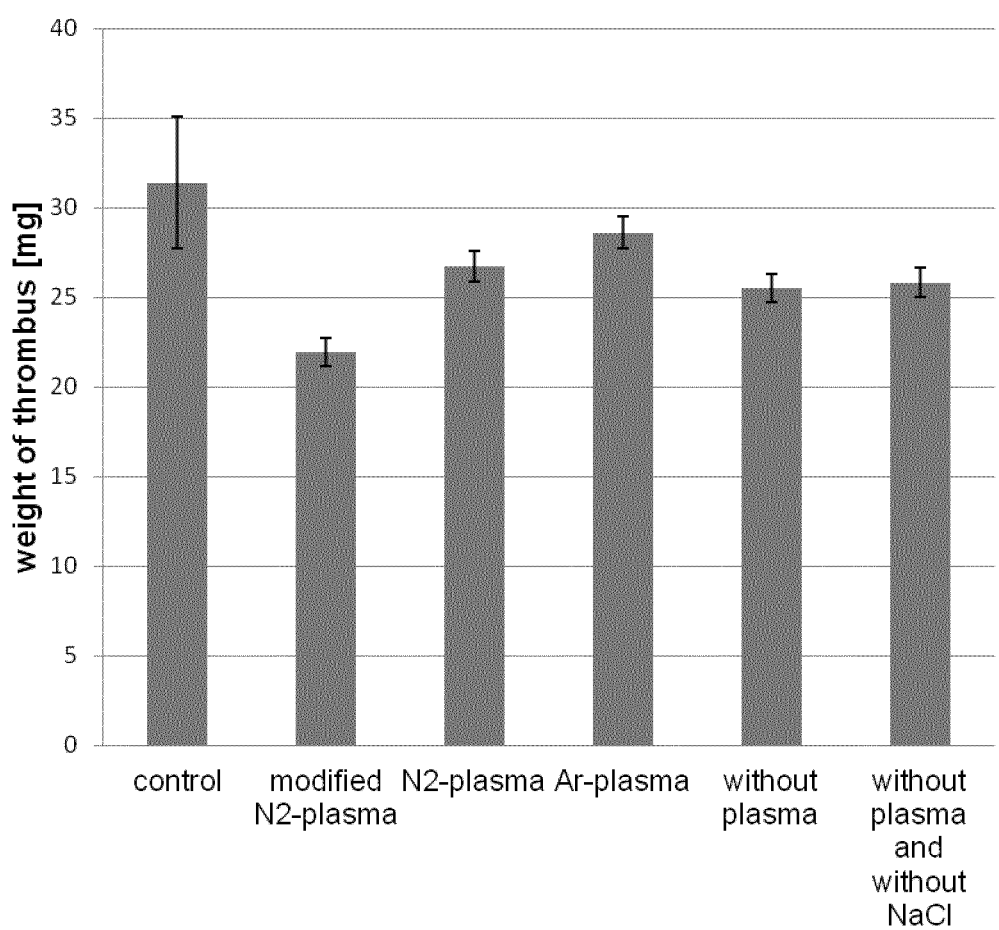
FIG. 12 shows a chart of the thrombus formation induced by PUR-AT III, wherein the PUR was treated with different plasmas before binding of AT III.

For the assay the discs were incubated with ETDA blood (reactivated by use of $CaCl_2$) for two days. During this time a thrombus could form on the surface of the discs. After the two days the discs were removed from the blood, washed thoroughly and weighed. The results obtained are shown in FIG. 12. The results show that the modification of the $N_2$-plasma by addition of $CO_2$ has a positive antithrombogenic effect on the PUR.

The invention claimed is:

1. An antithrombogenic polyurethane (PUR) having an antithrombogenic coating, wherein the antithrombogenic coating comprises at least one antithrombogenic substance covalently bound to a surface of the PUR via at least two bonds, wherein a first of said bonds is an amide bond between the surface of the PUR and a polyethyleneimine (PEI) and a second of said bonds is between the PEI and the antithrombogenic substance, wherein the surface of the PUR had been activated by use of a carbon dioxide plasma or a plasma modified by addition of carbon dioxide before the first of said bonds was formed.

2. PUR according to claim 1, wherein the PUR is an elastomeric PUR or an elastomeric polycarbonate based PUR.

3. PUR according to claim 2, wherein the PUR is synthesized from polycarbonate glycol, methylene diisocyanate, ethylene diamine, and diaminocyclohexane.

4. PUR according to claim 1, wherein the PEI is branched or a dendrimer.

5. PUR according to claim 1, wherein the second bond is an amide bond.

6. PUR according to claim 1, wherein the antithrombogenic substance is heparin modified to comprise a reactive group in unbound condition or antithrombin III (AT III) or any other antithrombogenic substance having at least one carboxy group, ketone group, aldehyde group or amino group in unbound condition.

7. PUR according to claim 1, wherein the modified plasma is a nitrogen plasma or an argon plasma.

8. PUR according to claim 1, comprising a medicament comprised of the PUR.

9. PUR according to claim 1, comprising a medicament or medical device comprised of the PUR adapted for use in the treatment of thrombosis or a risk of getting thrombosis.

10. A medical device adapted to be inserted or contacted temporarily or permanently into or with a bloodstream or adapted to be inserted temporarily or permanently into a body of a mammal or a human being, wherein a surface of said medical device comprises the PUR according to claim 1.

11. A method of producing an antithrombogenic polyurethane (PUR) comprising the following steps:
   a) activation of an antithrombogenic coating on a surface comprised of polyurethane PUR, wherein activation is performed by use of a plasma, and wherein i) the plasma is a carbon dioxide plasma, or ii) the plasma is modified by addition of carbon dioxide,
   b) a first coupling, wherein a polyethyleneimine (PEI) is coupled to the PUR surface, and
   c) a second coupling, wherein at least one antithrombogenic substance is coupled to the PEI,
to produce an antithrombogenic PUR surface, the antithrombogenic surface comprised of at least one antithrombogenic substance covalently bound to a surface of the PUR via at least two bonds, wherein a first of said bonds is an amide bond between the surface of the PUR and a PEI and a second of said bonds is between the PEI and the antithrombogenic substance.

12. Method according to claim 11, wherein the PUR surface is exposed to air or oxygen between steps a) and b).

13. Method according to claim 12, wherein the PUR surface is incubated in water, a buffer, a saline solution, or an isotonic saline solution between steps a) and b).

14. Method according to claim 11, wherein the first coupling or the second coupling is performed by use of N-Hydroxysuccinimide (NHS) and N,N'-Dicyclohexylcarbodiimide (DCC) or 1-Ethyl-3-(3-dimethylaminopropyl)carbodiimide (EDC).

15. Method according to claim 14, wherein the modified plasma is a nitrogen plasma or an argon plasma.

16. Method according to claim 11, wherein the first and the second coupling is performed by use of N-Hydroxysuccinimide (NHS) and N,N'-Dicyclohexylcarbodiimide (DCC) or 1-Ethyl-3-(3-dimethylaminopropyl)carbodiimide (EDC).

17. Method according to claim 13, wherein the PUR surface is exposed to air or oxygen between steps a) and b) after the exposure to air or oxygen.

18. Method according to claim 11, wherein the PUR surface is incubated in water, a buffer, a saline solution, or an isotonic saline solution between steps a) and b).

19. Method according to claim 11, wherein the modified plasma comprises a nitrogen plasma or an argon plasma.

20. Method according to claim 11, wherein the PUR is formed into a medicament or a medical device adapted for use in a bloodstream.

* * * * *